US006702762B2

(12) United States Patent
Jafari et al.

(10) Patent No.: US 6,702,762 B2
(45) Date of Patent: Mar. 9, 2004

(54) APPARATUS AND METHOD FOR JOINING TWO GUIDE WIRE CORE MATERIALS WITHOUT A HYPOTUBE

(75) Inventors: Mo Jafari, Murrieta, CA (US); David H. Burkett, Temecula, CA (US); Edwin P. Mahieu, Temecula, CA (US); Brad Kellerman, Escondido, CA (US)

(73) Assignee: Advanced Cardiovascular Systems, Inc.

( * ) Notice: Subject to any disclaimer, the term of this patent is extended or adjusted under 35 U.S.C. 154(b) by 76 days.

(21) Appl. No.: 10/032,873

(22) Filed: Dec. 27, 2001

(65) Prior Publication Data

US 2003/0125641 A1 Jul. 3, 2003

(51) Int. Cl.⁷ ............................. A61B 5/00; A61M 25/00
(52) U.S. Cl. ..................................................... 600/585
(58) Field of Search ................. 600/585, 508, 600/434, 486, 561; 403/224, 292, 293, 294, 298, 306, DIG. 4; 604/170.01, 531, 95.01, 164.13, 528, 533, 538

(56) References Cited

U.S. PATENT DOCUMENTS

| 4,827,941 A | | 5/1989 | Taylor et al. |
| 4,875,489 A | | 10/1989 | Messner et al. |
| 4,966,163 A | | 10/1990 | Kraus et al. |
| 5,213,111 A | | 5/1993 | Cook et al. |
| 5,341,818 A | | 8/1994 | Abrams et al. |
| 5,513,650 A | * | 5/1996 | Johansen ..................... 600/508 |
| 5,637,089 A | | 6/1997 | Abrams et al. |
| 5,853,375 A | * | 12/1998 | Orr ............................. 600/585 |
| 5,951,494 A | | 9/1999 | Wang et al. |
| 6,165,292 A | | 12/2000 | Abrams et al. |
| 6,248,082 B1 | | 6/2001 | Jafari |
| 6,280,539 B1 | | 8/2001 | Abrams et al. |
| 6,544,197 B2 | * | 4/2003 | DeMello ..................... 600/585 |

FOREIGN PATENT DOCUMENTS

| EP | 0 838 230 A2 | 4/1998 |
| WO | WO 91/15152 | 10/1991 |

OTHER PUBLICATIONS

Pacetti.: "MRI compatible guide wire", U.S. patent application Ser. No. 10/034,715, filed Dec. 25, 2001.

* cited by examiner

*Primary Examiner*—Max F. Hindenburg
*Assistant Examiner*—Brian Szmal
(74) *Attorney, Agent, or Firm*—Fulwider Patton Lee & Utecht, LLP

(57) ABSTRACT

An intravascular guide wire having at least two core materials joined together without the use of a hypotube. There is a core having a proximal core section with a proximal end and a distal end and a distal core section with a proximal end and a distal end. The distal end of the proximal core section and the proximal end of the distal core section are ground into complementary shapes, and then placed into a fixture in opposing directions with a small gap in-between the ends to receive a mass of hardened material to wick therein. Once the proximal and distal core sections are bonded, welded, brazed, cemented, or soldered together, the guide wire is then ground to a required outer diameter, depending on the design needs of the specific guide wire.

39 Claims, 2 Drawing Sheets

APPARATUS AND METHOD FOR JOINING TWO GUIDE WIRE CORE MATERIALS WITHOUT A HYPOTUBE

BACKGROUND OF THE INVENTION

This invention relates to the field of medical devices, and more particularly to a guide wire for advancing a catheter within a body lumen in a procedure such as percutaneous transluminal coronary angioplasty (PTCA).

In a typical PTCA procedure, a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. A guide wire is first advanced by itself through the guiding catheter until the distal tip of the guide wire extends beyond the arterial location where the procedure is to be performed. Then a catheter is mounted onto the proximal portion of the guide wire which extends out of the proximal end of the guiding catheter which is outside of the patient. The catheter is advanced over the guide wire, while the position of the guide wire is fixed, until the operative element on the catheter is disposed within the arterial location where the procedure is to be performed. After the procedure is performed, the catheter may be withdrawn from the patient over the guide wire or the guide wire repositioned within the coronary anatomy for an additional procedure.

Conventional guide wires for angioplasty, stent delivery, atherectomy and other intravascular procedures usually have an elongate core member with one or more segments near the distal end thereof which taper distally to smaller cross sections. A flexible body member, such as a helical coil or a tubular body of polymeric material, is typically disposed about and secured to at least part of the distal portion of the core member. A shaping member, which may be the distal extremity of the core member or a separate shaping ribbon which is secured to the distal extremity of the core member, extends through the flexible body and is secured to the distal end of the flexible body by soldering, brazing or welding; or an adhesive may be used in the case of polymeric flexible bodies which forms a rounded distal tip. The leading tip is highly flexible and will not damage or perforate the vessel. The portion behind the distal tip is increasingly stiff, which better supports a balloon catheter or similar device.

A major requirement for guide wires is that they have sufficient column strength to be pushed through a patient's vascular system or other body lumen without kinking. However, they must also be flexible enough to avoid damaging the blood vessel or other body lumen through which thy are advanced. Efforts have been made to improve both the strength and flexibility of guide wires to make them more suitable for their intended uses, but these two properties are for the most part diametrically opposed to one another in that an increase in one usually involves a decrease in the other.

In order to fulfill these requirements, guide wires now include two different types of material joined together with a connecting tube, hypotube, or sleeve, so that a proximal core will consist of a material having sufficient column strength and a distal core will be made of a flexible material to advance through a body lumen. Currently, an expensive nitinol hypotube or connecting tube is used to join a proximal stainless steel core to a nitinol distal core on certain types of guide wires. An example of this type of guide wire can be seen in, for example, U.S. Pat. No. 6,248,082 (Jafari).

SUMMARY OF THE INVENTION

The present invention is directed to an intravascular guide wire having at least two core materials joined together without the use of a hypotube. In one embodiment, the invention provides a core having a proximal core section with a proximal end and a distal end and a distal core section with a proximal end and a distal end. It is preferred that the proximal core section is made of stainless steel to provide sufficient column strength, and the distal core section is made of nitinol which is flexible to advance through a tortuous body lumen. The distal end of the proximal core section and the proximal end of the distal core section are formed into a complementary shapes, and then placed into a fixture in opposing directions with a small gap in-between the ends. The small gap allows for a mass of hardened material to wick therein. Once the proximal and distal core sections are bonded together, the guide wire is ground to a required outer diameter depending on the design needs of the specific guide wire.

The geometric design of the distal end of the proximal core and the proximal end of the distal core ("the connecting ends") can be constructed using a variety of methods and can be shaped in a variety of designs. The methods for forming the complementary geometric shapes into the connecting ends include, but are not limited to, grinding, milling, electrical discharge machining (EDM), laser cutting, etc. Designs of the connecting ends can include a D-shape cross-sectional shape, or a D-shape cross-sectional shape with a backside of one of the connecting ends including a taper. Another embodiment includes a D-shape cross-sectional shape with a serration, and a taper may be added to the backside of this design as well. Yet another embodiment includes a tapered D-shaped cross-sectional shape. The connecting ends may also have locking serrations, where the locking serrations of the ends mechanically grip, clasp, or engage one another. These and other complementary interfacing shapes may be used at the connecting ends.

The mass of hardened material that is used to join the proximal and distal cores may be any bonding material, including the following: solder, brazes, epoxies, glues, laser welds, spot welds, etc. that are preferable for the wire type and provide the required functional attributes. Joining the two cores together can be accomplished by dispensing, for example, solder in-between the connecting ends and/or encasing the connecting ends with solder.

The present invention method of joining a proximal and a distal core section can be applied to any two wires, and to any guide wire having a diameter ranging from about 0.006 to 0.040 inch. Wire materials that may be combined through this method include, but are not limited to, all types of metals, alloys, polymers, and composite materials.

The present invention can also be used to create a guide wire with two lap joints. One joint would connect the proximal core section to the distal core section, and the second joint would connect a shaping ribbon to the distal end of the distal core section.

These and other advantages of the invention will become more apparent from the following detailed description thereof and the accompanying exemplary drawings.

DETAILED DESCRIPTION OF THE PREFERRED EMBODIMENTS

Figure 1:
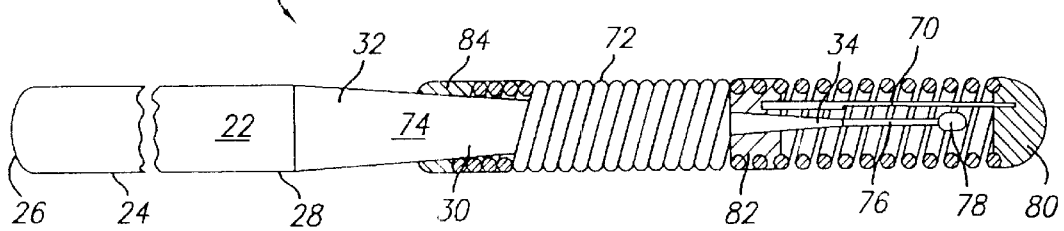
FIG. 1 is a side elevational view showing one embodiment of the present invention guide wire with two sections connected without the use of a hypotube.

The present invention is directed to a guide wire that uses at least two core materials that are joined at an interface without the use of a sleeve or hypotube at the joint. FIG. 1 illustrates in a side elevational view one embodiment of the present invention guide wire, generally designated 20, that is adapted for insertion into a patient's body lumen, such as an artery or vein. In this embodiment, the intravascular guide wire 20 has at least two core materials joined or secured together without the use of a hypotube, connecting tube, or sleeve. In particular, the guide wire 20 has a core 22 with a proximal core section 24 having a proximal end 26 and a distal end 28 and a distal core section 30 having a proximal end 32 and a distal end 34. It is preferred that the proximal core section 24 is made of stainless steel, and the distal core section 30 is made of nitinol. However, the core sections may be made out of any material known in the guide wire art.

In the embodiment as shown in FIG. 1, the guide wire 20 also includes a shapeable member 70 which can be secured to the distal end 30 by a solder or weld bead 82, and a flexible body 72 such as a helical coil. Preferably, the flexible body 72 is disposed about and secured to the distal core section 30 by a solder or weld bead 84. The distal core section 30 has an optional tapered core segment 74 and an optional flexible core segment 76 which is distally contiguous to the tapered core segment. At the very distal end of the flexible core segment 76 is a rounded distal extremity 78. Of course, the rounded distal extremity 78 may be of other shapes and sizes, can be flattened, or omitted altogether. In fact, in an alternative embodiment core-to-tip design, the core segment 76 extends continuously to engage a rounded tip 80 at the very distal end of the guide wire 20.

Figure 3:
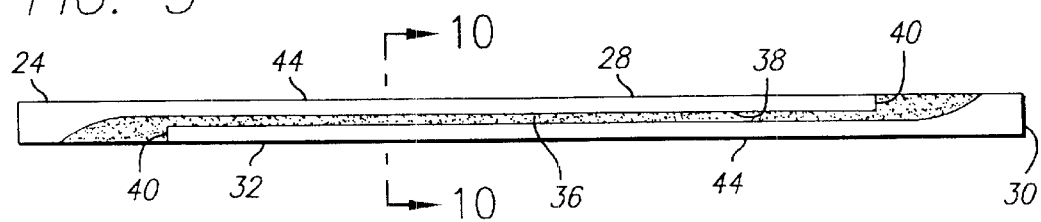
FIG. 3 is a partial, side elevational view depicting the complementary distal end of the proximal core section and the proximal end of the distal core section, aligned with one another with a gap therebetween.
Figure 4:
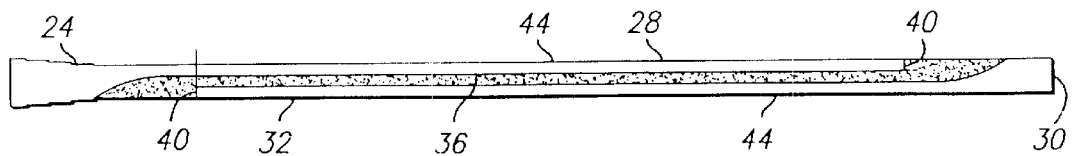
FIG. 4 is a partial, side elevational view of the guide wire shown in FIG. 3 with the outer diameter having been ground down.

The distal end 28 of the proximal core section 24 and the proximal end 32 of the distal core section 30, now referred to as the connecting ends 28 and 32, are aligned with one another. The connecting ends 28, 32 have complementary shapes as seen in FIG. 3. That is, in the embodiment shown, the connecting ends 28, 32 have respective elongated cut-outs or chamfers that engage each other. The complementary cut-outs provide a constant, low profile outside diameter along the joint. Moreover, the elongated overlap at the joint presents a large surface area for a bond, weld, etc. to adhere to thus improving the strength of the joint. Furthermore, the large overlap ensures efficient torque transmission from the proximal core section 24 to the distal core section 30.

A mass of hardened material 36 disposed between the connecting ends 28, 32, and/or encase the connecting ends. The mass of hardened material 36 is a bonding material such as, but not limited to, solders, brazes, epoxies, glues, welds including laser welds and spot welds. It is preferred that solder is used to form a joint between the connecting ends 28 and 32, and that the solder include SnAg 95-5 along with NiTi flux 400. However, any type of compatible solder having the proper strength to bond core materials together could be used, such as other ratios of silver-tin solder, including 90-10, and also gold-tin solder may be used. Tests show that the joint formed with solder is generally twice as strong as a joint formed using a hypotube.

Figure 2:
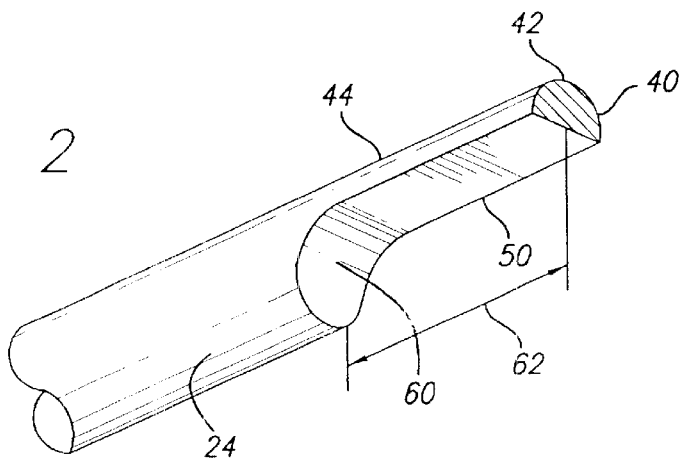
FIG. 2 is a partial perspective view of the tip of a D-shaped distal end of one of the core sections of the guide wire.
Figure 10:
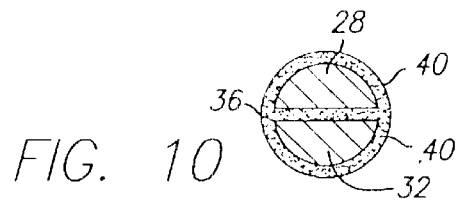
FIG. 10 is a cross-sectional view taken along line 10—10 in FIG. 3 showing the distal end of the proximal core section and the proximal end of the distal core section encased in solder.

In the embodiment as seen in FIGS. 2, 3, and 10, the complementary shape of the connecting ends 28 and 32 is a D-shape cross-section 40. As seen in the cross-sectional view of FIG. 10, the D-shape has a semicircular shape with a straight edge. Other cross-sectional shapes such as ovoids, triangles, trapezoids, rectangles, and similar polygons are contemplated.

FIG. 2 shows the cantilevered tip 42 of the distal end 28 of the proximal core section 24 which has been formed into a D-shape 40. The connecting ends 28 and 32 can be seen in FIG. 3 connected together with each end having a D-shape cross-section 40. In this embodiment, a cantilevered portion 62 of the D-shaped cross-section 40 extends preferably 1 cm long and transitions into the circular cross-sectional shape of the proximal core section 24. A transition 60 can be a gradual curved as shown in FIG. 2, or it may be a step or more angular in profile. In other embodiments, the length of the cantilevered portion 62 can range from 1 mm to 5 cm as needed for optimal design functionality. Naturally, the length of the cantilevered portion 62 influences amount of interfacing surface area available to be welded, bonded, soldered, etc.

Figure 5:
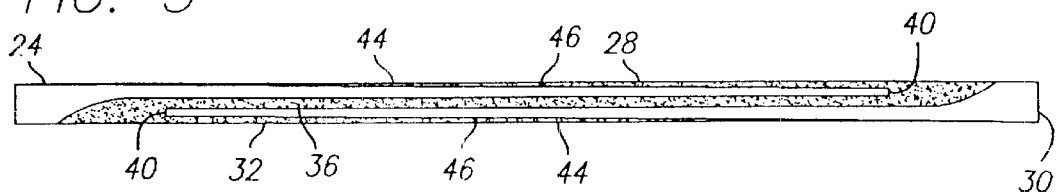
FIG. 5 is a partial, side elevational view of the guide wire in FIG. 3 with tapered backsides.

Another embodiment is seen in FIG. 5, where the complementary shape of the connecting ends 28 and 32 has a D-shaped cross-section 40 with a backside 44 on each of the D-shaped ends having a taper 46. In this embodiment, the outside diameter of the joint is not constant along its length, especially at the tips of the proximal end 32 of the distal core section 30 and distal end 28 of the proximal core section 24. It is also possible to have only one of the connecting ends 28 or 32 with the tapered backside 46. This design eliminates a potential for the ends to "peel" apart during a tight bend, and provides a more flexible end that easily bends. In addition, the design of the tapered backside 46 allows for a hardened material 36 such as solder to at least partially envelope the ends 28 and 32, which also reduces peel potential.

Figure 6:
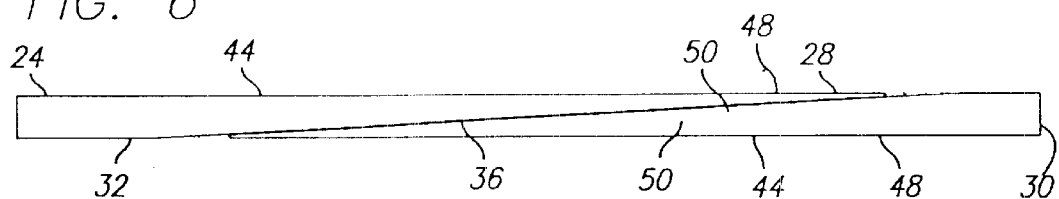
FIG. 6 is a partial, side elevational view of the distal end of the proximal core section and the proximal end of the distal core section having a tapered D-shape.

Yet another embodiment is shown in FIG. 6, where the connecting ends 28 and 32 include a tapered, D-shaped cross-section 48. The taper in this embodiment is disposed on a front-side 50 of the D-shape cross-section 48, and it is possible for only one of the connecting ends 28 or 32 to include this tapered D-shaped cross-section 48. In one embodiment, the tapered, D-shaped cross-section 48 which is ground into the connecting ends 28 and 32 is 3 cm in length, although the length may range from 1 cm–5 cm. The FIG. 6 embodiment provides a more gradual transition from the proximal core section 24 to the distal core section 30 and therefore is beneficial when using wires with dissimilar bending forces. It is also conceivable to have another embodiment, where both the front and back sides of the connecting ends have a taper, such that the distal end of the proximal core section has opposed, imaginary planes converging in a proximal direction, and the proximal end of the distal core section has opposed, imaginary planes converging in a distal direction.

Figure 7:
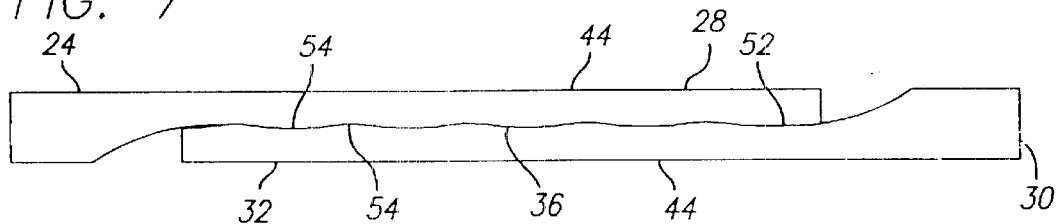
FIG. 7 is a partial, side elevational view of the distal end of the proximal core section and the proximal end of the distal core section wherein the interfacing surfaces are serrated.
Figure 8:
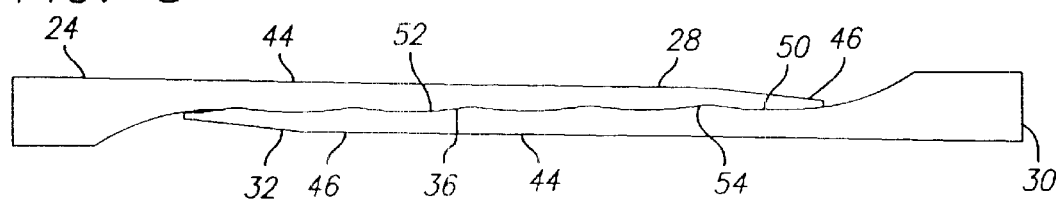
FIG. 8 is a partial, side elevational view of the guide wire in FIG. 7 with a tapered backside.

FIG. 7 shows another embodiment where the connecting ends 28 and 32 include a serrated profile 52 at the interface where the ends engage. The serrations 54 provide an alignment geometry that creates improved joint strength due to the more complex interface, some frictional engagement, and additional gaps into which the mass of hardened material 36, such as solder, can flow. The serrations 54 improve overall column strength at the joint as well as providing good flexibility for bending. These attributes further reduce the potential for the joint to peel apart under stress. This embodiment can also be enhanced by adding a taper 46 on the backside 44 of the serrated D-shaped ends 28, 32 as shown in FIG. 8.

Figure 9:
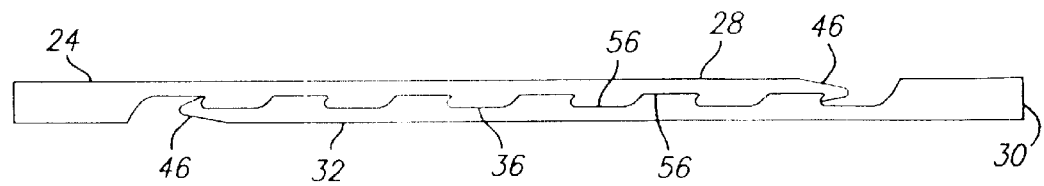
FIG. 9 is a partial, side elevational view of the distal end of the proximal core section and the proximal end of the distal core section wherein the interfacing surfaces have locking serrations.

As seen in FIG. 9, another embodiment has locking serrations 56 formed on the connecting ends 28 and 32 that mechanically engage and grip one another. This embodiment has the attribute of allowing unbonded fitment of the locking serrations 56 before the bonding process, which eliminates the need for unique alignment fixtures that keep the cores appropriately aligned for soldering or bonding. That is, the serrations 56 of the connecting ends 28, 32 have complementary teeth that mechanically interlock without using any bonding or adhesive agents, which agents are added later to permanently cement the parts to one another. The mechanical interlock obviates the need for customized fixtures, but enables precise alignment of the parts to be joined.

Next, a method of constructing the above embodiments of the present invention guide wire 20 without a hypotube or sleeve will be discussed. In one embodiment, one of the complementary shapes described above or any other complementary shape is formed into the connecting ends 28 and 32 by grinding, milling, electrical discharge machining (EDM), laser cutting, or any other appropriate method known in the art. If required, an additional step may be taken where the grind on the connecting ends 28 and 32 is gold tinned or etched for improved solderability. After the connecting ends 28 and 32 have been ground into the desired shape, the proximal and distal core sections 24 and 30 are then placed in a fixture in opposing directions with the connecting ends overlapping each other. The core sections 24 and 30 are placed in the fixture so that there is a small gap 38 between the connecting ends 28 and 32 for solder, or other bonding material, to wick into, and then bond and secure the two core sections together. The solder or other bonding material may also encase the connecting ends 28 and 32 to provide a stronger bond. Then, the joined proximal and distal core sections 24 and 30 are ground to a required outer diameter. The actual final grind diameter depends upon the design needs of the specific guide wire. Once the final grind is complete, an optional polymer coating may then be applied to at least a portion of or the entire the core 22. The finished guide wire has a smooth cross-sectional profile at the joint from the proximal core section 24 to the distal core section 30.

There are several additional steps that can be taken to improve the joint integrity of the guide wire 20. If greater bond strength is required, the connecting ends 28 and 32 can be plunge ground to a smaller diameter prior to or following the forming of the complementary shape. For instance, a 0.0130 inch diameter would be plunge ground to 0.010 inch. This smaller diameter allows the solder or other bonding material to be applied around the entire circumference of the joined cores 24 and 30. FIG. 10 shows a cross-sectional view, taken along line 10—10 of FIG. 3, of the connecting ends 28 and 32 having D-shaped cross-section 40 which have been plunge ground to a smaller diameter so the mass of hardened material 36, for example solder, encases the entire circumferences of the cores 24 and 30. In fact, the D-shaped cross-section 40 is optionally ground to about one half the diameter of the guide wire core 22 or slightly less. Also, as already discussed, the backsides 44 of the complementary shaped connecting ends 28 and 32 can be ground to form a taper 46. This feature provides a more flexible end that bends instead of peeling apart, and it allows for more solder to encompass the end.

To provide a gradual transition form the proximal core to the distal core, the tapered D-shaped cross-section 40 may be ground into the connecting ends 28 and 32. Likewise, serrations 54 may be formed by grinding.

In yet another method according to the present invention, the connecting ends 28 and 32 are plunge ground to provide a constant or tapered smaller diameter. In one embodiment, this constant or tapered smaller diameter is approximately 1 cm long, but may be 0.5 to 5 cm long. If required, an additional step may be taken where the plunge grind on the ends 28 and 32 is then tinned or etched for improved solderability. The plunge ground cores 24 and 30 are then placed in a fixture in opposing directions so that the connecting ends 28 and 32 overlap one another. Next, solder or other bonding material is applied along the overlap to join to the two cores 24 and 30. The joined cores 24 and 30 are then ground to a required outer diameter. This final grind diameter is dependent upon the design needs of the specific guide wire. Once the final grind is complete, a polymer coating may then be applied to the core 22 or the guide wire 20.

There is no change to how a guide wire produced with the disclosed methods is used. The methods described produce a guide wire with at least two core sections which are joined together without the use of a hypotube or sleeve. Also these methods may be used to join any two wires together, and may even be used to attach a shaping ribbon onto the distal end of the distal core section, producing a guide wire with two lap joints. This embodiment includes at least three core materials that are joined or bonded together in the same manner as previously described for a single lap joint of two core materials. One embodiment would include a first lap joint connecting together a stainless steel section with a nitinol section, and the second lap joint connecting the nitinol section with another stainless steel section that can then be formed to act as a shaping ribbon. After the two lap joints are formed, the assembly is ground to appropriate dimensions. Further, any wire can be formed containing any number of core materials or any number of lap joints using this method.

While a particular form of the invention has been illustrated and described, it will also be apparent to those skilled in the art that various modifications can be made without departing from the spirit and scope of the invention. It should be clear that the types of material used in the core sections may vary. Also, the size and dimensions of the guide wire can vary in terms of outer diameter, ground diameter, length, and ground length. Accordingly, it is not intended that the invention be limited except by the appended claims.

What is claimed is:

1. An intravascular guide wire, comprising:
   a core having a proximal core section with proximal and distal ends and a distal core section with proximal and distal ends; and
   a mass of hardened material at a joint connecting the distal end of the proximal core section to the proximal end of the distal core section;
   wherein the joint is not covered by a sleeve.

2. The guide wire of claim 1, wherein at least one of the distal end of the
   proximal core section and the proximal end of the distal core section have a D-shape cross-sectional shape.

3. The guide wire of claim 1, wherein a backside of one of the distal end of the proximal core section and the proximal end of the distal core section includes a taper.

4. The guide wire of claim 1, wherein at least one of the distal end of the proximal core section and the proximal end of the distal core section includes a serration.

5. The guide wire of claim 1, wherein at least one of the distal end of the proximal core section and the proximal end of the distal core section includes a rounded cross-section having a straight edge.

6. The guide wire of claim 1, wherein at least one of the distal end of the proximal core section and the proximal end of the distal core section includes a front side including a taper.

7. The guide wire of claim 1, wherein the distal end of the proximal core section and the proximal end of the distal core section have locking serrations, and the locking serrations of the ends grip one another.

8. The guide wire of claim 1, wherein at least one of the distal end of the proximal core section and the proximal end of the distal core section includes gold tin disposed thereon.

9. The guide wire of claim 1, wherein at least one of the distal end of the proximal core section and the proximal end of the distal core section has been etched.

10. The guide wire of claim 1, wherein the mass of hardened material includes a bonding material selected from the group consisting of: solders, brazes, epoxies, glues, laser welds, or spot welds.

11. The guide wire of claim 1, wherein the mass of hardened material is disposed in-between the distal end of the proximal core section and the proximal end of the distal core section.

12. The guide wire of claim 1, wherein the mass of hardened material is disposed in-between the distal end of the proximal core section and the proximal end of the distal core section encasing the ends.

13. An intravascular guide wire having at least two core materials joined together without the use of a hypotube, comprising:
    a core having a proximal core section with a proximal end and a distal end and a distal core section with a proximal end and a distal end;
    the distal end of the proximal core section and the proximal end of the distal core section being aligned complementary to one another; and
    a mass of hardened material disposed between the distal end of the proximal core section and the proximal end of the distal core section;
    wherein the at least two core materials are joined together without the use of a hypotube.

14. The guide wire of claim 13, wherein at least one of the distal end of the proximal core section and the proximal end of the distal core section have a D-shape cross-sectional shape and a backside of one of the D-shape cross-sectional shape ends includes a taper.

15. The guide wire of claim 13, wherein at least one of the distal end of the proximal core section and the proximal end of the distal core section have a D-shape cross-sectional shape including a serration.

16. The guide wire of claim 15, wherein at least one of the distal end of the proximal core section and the proximal end of the distal core section includes a rounded cross section having a straight edge.

17. The guide wire of claim 13, wherein at least one of the distal end of the proximal core section and the proximal end of the distal core section includes a D-shaped cross-sectional shape including a taper.

18. The guide wire of claim 13, wherein the distal end of the proximal core section and the proximal end of the distal core section have locking serrations, and the locking serrations of the ends grip one another.

19. The guide wire of claim 13, wherein the mass of hardened material includes a bonding material selected from the group consisting of: solders, brazes, epoxies, glues, or welds.

20. The guide wire of claim 13, wherein the mass of hardened material encases the distal end of the proximal core section and the proximal end of the distal core section.

21. A method for joining two intravascular guide wire core materials without using a hypotube, comprising:
    providing a proximal core section with a proximal and distal end and a distal core section with a proximal and distal end;
    forming a complementary shape into the distal end of the proximal core section and the proximal end of the distal core section;
    positioning the proximal and distal core sections in opposing directions;
    leaving a gap in-between the distal end of the proximal core section and the proximal end of the distal core section; and
    disposing in the gap a mass of material joining the proximal and distal core sections together;
    wherein the guide wire core materials are joined together without the use of a hypotube.

22. The method of claim 21, further comprising grinding the joined proximal and distal core sections to a desired diameter.

23. The method of claim 21, wherein the complementary shapes include a D-shape.

24. The method of claim 21, further comprising tapering a backside of at least one of the distal end of the proximal core section and the proximal end of the distal core section.

25. The method of claim 21, further comprising serrating the distal end of the proximal core section and the proximal end of the distal core section.

26. The method of claim 25, further comprising tapering a backside of at least one distal end of the proximal core section and the proximal end of the distal core section.

27. The method of claim 21, wherein the complementary shape includes a tapered D-shape.

28. The method of claim 21, wherein the complementary shaped ends include locking serrations.

29. The method of claim 28, further comprising engaging the locking serrated ends together.

30. The method of claim 21, wherein the complementary shape is formed by a process consisting of: grinding, laser machining, electrical discharge machining, or chemical etching.

31. The method of claim 21, further comprising gold tinning the complementary shaped ends.

32. The method of claim 21, further comprising etching the complementary shaped ends.

33. The method of claim 21, further comprising plunge grinding the distal end of the proximal core section and the proximal end of the distal core section prior to forming the complementary shaped ends.

34. The method of claim 21, further comprising plunge grinding the distal end of the proximal core section and the proximal end of the distal core section after forming the complementary shaped ends.

35. A method for joining at least two intravascular guide wire core materials without using a hypotube, comprising:
   providing a proximal core section with a proximal and distal end and a distal core section with a proximal and distal end;
   plunge grinding at least one of the distal end of the proximal core section and the proximal end of the distal core section;
   positioning the proximal and distal core sections in opposing directions;
   leaving an overlap between the distal end of the proximal core section and the proximal end of the distal core section;
   applying a hardening material along the overlap; and
   grinding the joined guide wire cores to a desired diameter;
   wherein the guide wire core materials are joined together without using a hypotube.

36. An intravascular guide wire, comprising:
   a core having a proximal core section with a proximal end and a distal end and a distal core section with a proximal end and a distal end;
   the distal end of the proximal core section and the proximal end of the distal core section having respective complementary surfaces engaging one another; and
   means for permanently joining the proximal and distal core sections together, without using a sleeve.

37. An intravascular guide wire, comprising:
   a core having a proximal core section with proximal and distal ends and a distal core section with proximal and distal ends; and
   a mass of material having sufficient strength to bond the proximal core section to the distal core section being disposed at a joint between the distal end of the proximal core section and the proximal end of the distal core section.

38. The guide wire of claim 37, wherein the joint has a smooth and constant cross-section from the proximal core section to the distal core section.

39. A method for joining at least two intravascular guide wire core materials, comprising:
   providing a proximal core section with a proximal and distal end and a distal core section with a proximal and distal end;
   forming a complementary shape into the distal end of the proximal core section and the proximal end of the distal core section;
   positioning the proximal and distal core sections in opposing directions;
   leaving a gap in-between the distal end of the proximal core section and the end of the distal core section; and
   disposing in the gap a mass of material having sufficient strength to bond the proximal core section to the distal core section.

* * * * *